United States Patent [19]

Bozek

[11] Patent Number: 4,836,017
[45] Date of Patent: Jun. 6, 1989

[54] METHOD AND APPARATUS FOR DETERMINING OIL CONTENT OF OIL WELL PRODUCTION

[75] Inventor: Daryn S. Bozek, Lloydminster, Canada

[73] Assignee: Universal Industries Ltd., Lloydminster, Canada

[21] Appl. No.: 59,668

[22] Filed: Jun. 8, 1987

[51] Int. Cl.⁴ .............................................. C21B 47/00
[52] U.S. Cl. ..................................... 73/155; 73/61.1 R
[58] Field of Search .................. 73/155, 61.1 R, 61 R, 73/861.04; 166/250

[56] References Cited
U.S. PATENT DOCUMENTS

| | | | |
|---|---|---|---|
| 3,277,710 | 10/1966 | Ball | 73/61.1 R X |
| 3,357,236 | 12/1967 | Kasten | 73/61.1 R X |
| 3,971,248 | 7/1976 | Christensen | 73/61.1 R |
| 4,429,273 | 1/1984 | Mazzagatti | 73/61.1 R X |
| 4,429,581 | 2/1984 | Furmaga | 73/155 X |
| 4,461,172 | 7/1984 | McKee et al. | 166/250 X |
| 4,573,346 | 3/1986 | Zacharias, Jr. | 73/61.1 R |
| 4,596,136 | 6/1986 | Zacharias | 73/861.04 X |
| 4,616,700 | 10/1986 | Wood et al. | 166/250 |
| 4,689,989 | 9/1987 | Aslesen et al. | 73/861.04 X |
| 4,720,998 | 1/1988 | Hogue | 73/61 R X |

FOREIGN PATENT DOCUMENTS

| | | |
|---|---|---|
| 461937 | 12/1949 | Canada . |
| 731303 | 3/1966 | Canada . |
| 751637 | 1/1967 | Canada . |
| 752121 | 2/1967 | Canada . |
| 808910 | 3/1969 | Canada . |
| 824958 | 10/1969 | Canada . |

Primary Examiner—Eugene R. LaRoche
Assistant Examiner—Seung Ham
Attorney, Agent, or Firm—Indyk Pojunas Brady

[57] ABSTRACT

A method of measuring the oil content in the gross oil production of an oil well in which the percentage of solids content thereof is known, comprises the steps of introducing a predetermined weight of well production into said vessel, determining the time interval required to introduce said predetermined weight of well production into said vessel, determining the total well production flow rate of said well production into said vessel during said time interval, electromagnetically determining the percentage water content in said well production, determining from said percentage water content the water flow rate into said vessel during said time interval, determining from said known percentage solids content the solids flow rate into said vessel during said time interval, and determining the percentage oil content in said well production by deducting said solids flow rate and said water flow rate from said total well production flow rate.

31 Claims, 8 Drawing Sheets

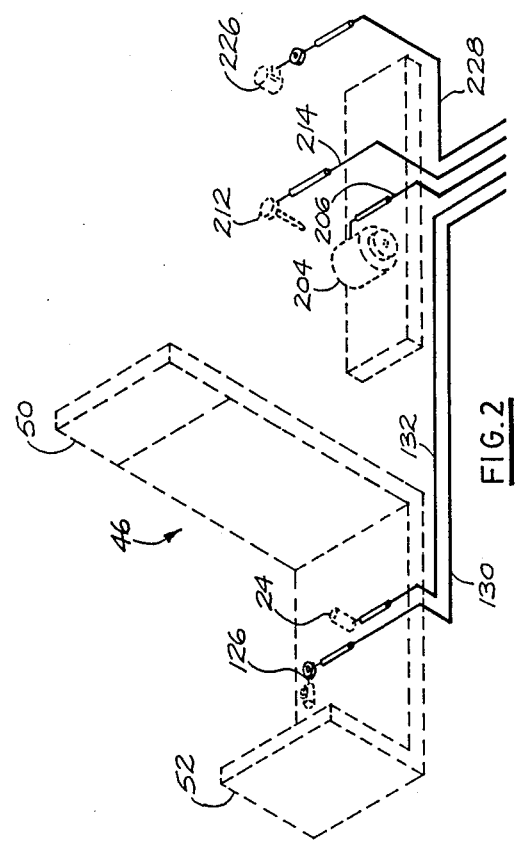
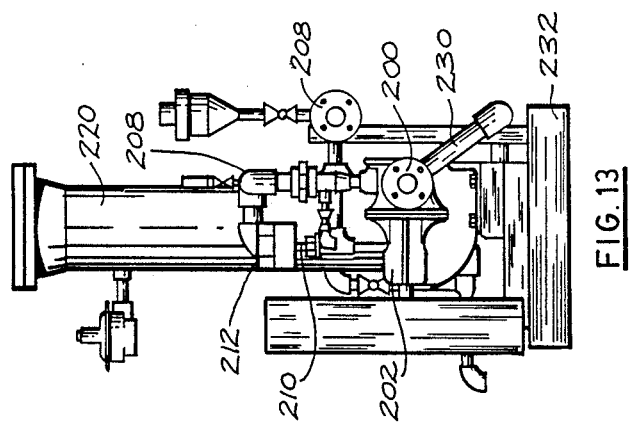

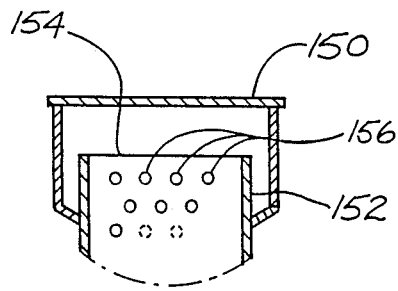
FIG. 8B
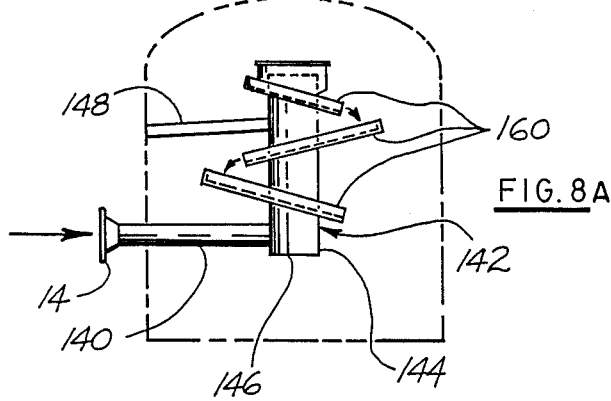
FIG. 8A
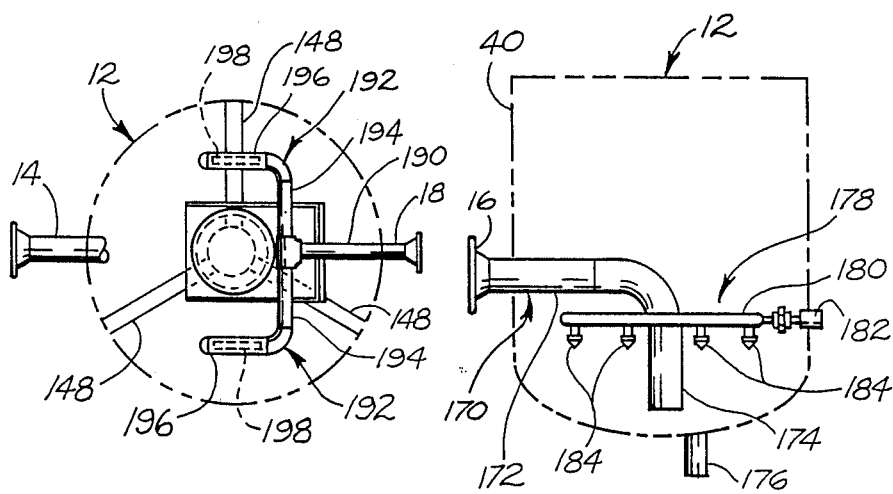
FIG. 9
FIG. 10

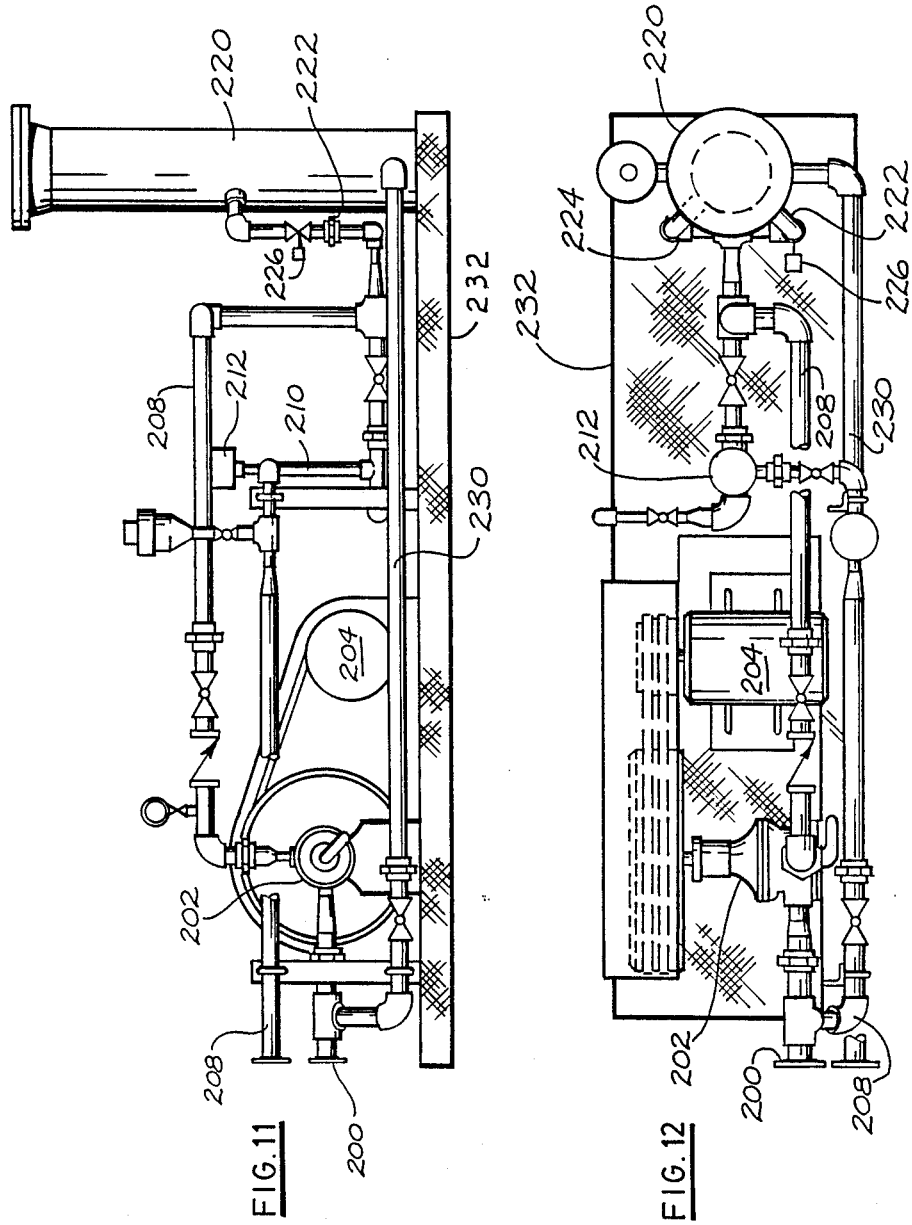

METHOD AND APPARATUS FOR DETERMINING OIL CONTENT OF OIL WELL PRODUCTION

The present invention relates to a method and apparatus for determining the percentage oil content produced by an oil well.

BACKGROUND OF THE INVENTION

In the oil industry, there are two measurements which are of concern when attempting to determine oil produced by an oil well. The first being is the gross production of the oil well and the second is the percentage of oil content in gross production.

In order to determine gross production, it is conventional to employ a "paddle wheel" mechanism in the well production flow stream. The rotational velocity of the paddle is monitored and used in calculation to obtain a gross production figure.

In order to determine the percentage oil content from the gross production, it was conventional to manually sample the well production; however, in recent years automated systems have been developed to facilitate this process. Some known systems use a test vessel in which a constant volume of liquid is admitted and monitored by a float arrangement. The test vessel is mounted on a monitoring mechanism calibrated according to the density of water. The difference in output between a predetermined volume of water and an equal volume of well production is a measure of the percentage oil content of the well output. Other automated systems use a probe to detect the changes in the oil-water ratio by means of a "dielectric constant" effect.

Heavy oil has a solids content often in excess of 15% and is of a much greater viscosity than conventional oil. The above described measurement systems suffer from significant drawbacks. For example, the paddle wheel arrangement tends to become clogged with heavy oil. The constituent elements of the heavy oil tend to stratify in the sample container giving different results depending upon the depth from which a sample is taken. Further, all known automated systems require some form of solids filtration. It is not practical to filter solids out of heavy oil production, the heavy oil will either not flow through or will rapidly destroy any known filtration mechanism. In addition, the build up of solids upon any test probe or testing vessel used will, over time, inevitably result in a distortion of the data obtained.

SUMMARY OF THE INVENTION

The primary object of the present invention is to provide a method and an apparatus which mitigate the drawbacks of the prior art.

Broadly, in accordance with one aspect of the present invention, there is provided a method of measuring the oil content in the gross oil production of an oil well in which the percentage of solids content thereof is known, the method comprising the steps of:

a. introducing a predetermined weight of well production into the vessel;

b. determining the time interval required to introduce the predetermined weight of well production into the vessel;

c. determining the total well production flow rate of the well production into the vessel during the time interval;

d. electromagnetically determining the percentage water content in the well production;

e. determining from the percentage water content the water flow rate into the vessel during the time interval;

f. determining from the known percentage solids content the solids flow rate into the vessel during the time interval; and g. determining the percentage oil content in the well production by deducting the solids flow rate and the water flow rate from the total well production flow rate.

In accordance with another aspect of the present invention, there is provided an apparatus for measuring the production of oil in the gross production of an oil well where the percentage of solids content of the gross oil production of the well is known, the apparatus comprising a pressure vessel having a well production inlet adapted to be connected to a feeder pipeline originating from one or more oil wells and a well production outlet for discharging well production from the vessel, means for subjecting a sample of the contents in the vessel to a predetermined electromagnetic signal and producing an electrical output signal representative of the percentage water content of the contents of the vessel, means for admitting a predetermined weight of well production into the vessel and producing a signal representative of fluid flow rate of the predetermined weight of well production into the vessel, and means responsive to the signal representative of fluid flow rate, the electrical output signal representative of the percentage water content and a signal representative of the known percentage solids content for producing in output representative of the percentage oil content of oil in the contents of the vessel.

BRIEF DESCRIPTION OF THE DRAWINGS

These and other features of the invention will become more apparent from the following description in which reference is made to the appended drawings, wherein:

FIG. 2 is a schematic drawing illustrating an electrical control system according to a preferred embodiment of the invention;

FIG. 8A is a partially broken cross-sectional view of the upper end portion of the vessel illustrating means by which well production introduced into the vessel is degassed and agitated;

FIG. 8B is a detailed view of FIG. 8A.

FIG. 9 is a transverse cross-section view of the vessel illustrating the well production discharge head disposed within and secured to the vessel;

FIG. 10 is a partially broken cross-sectional view of the lower end portion of the vessel illustrating means for discharging well production from the vessel and means for flushing and desanding the vessel; and FIGS. 11 and 12 are front and top views, respectively, of an apparatus, mounted on a skid assembly, for determining the percentage water content of a sample of the well production taken from the vessel.

FIG. 13 is a side elevation view of an apparatus, mounted on a skid assembly, for determining the percentage of water content of a sample of the well production taken from the vessel.

DESCRIPTION OF PREFERRED EMBODIMENT

Figure 1:
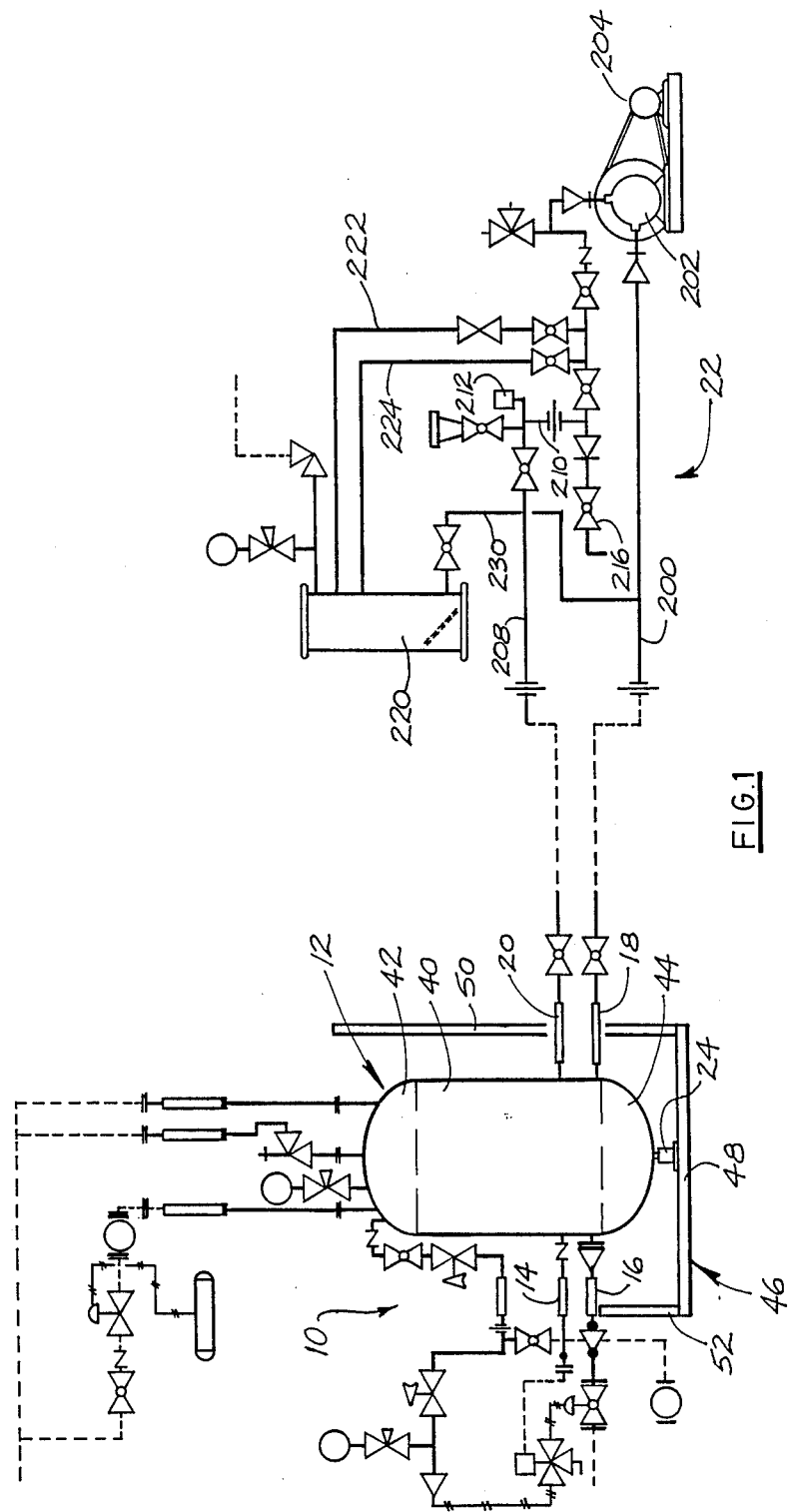
FIG. 1 is a schematic representation of a preferred embodiment of the present invention.
Figure 3:
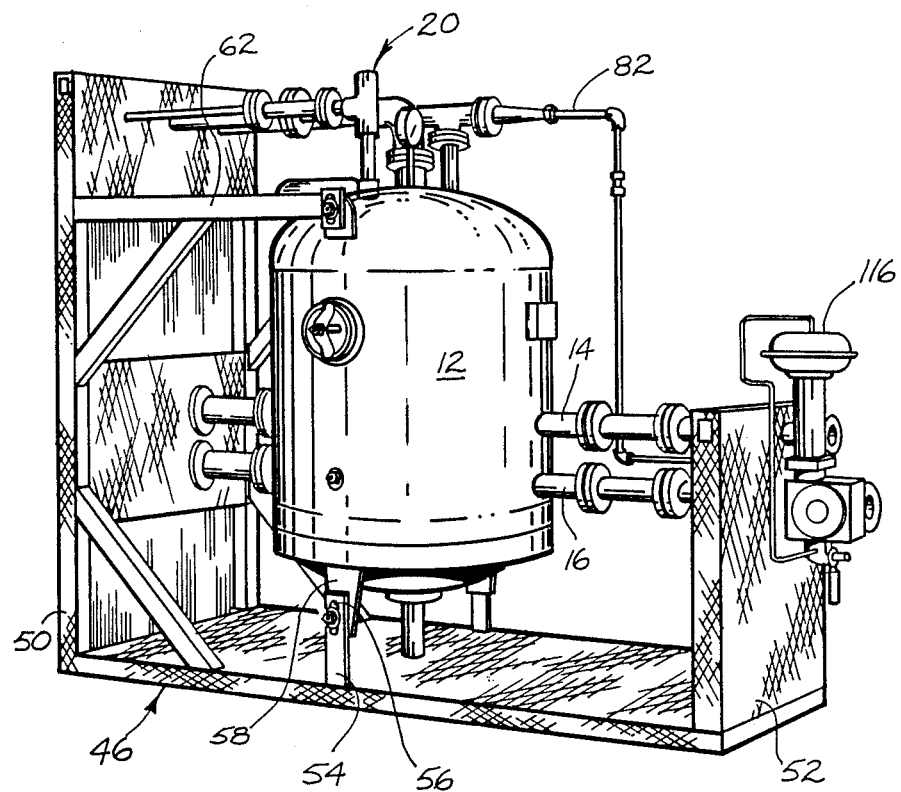
FIG. 3 is a perspective view of a pressure vessel and associated components for holding well production sample.
Figure 4:
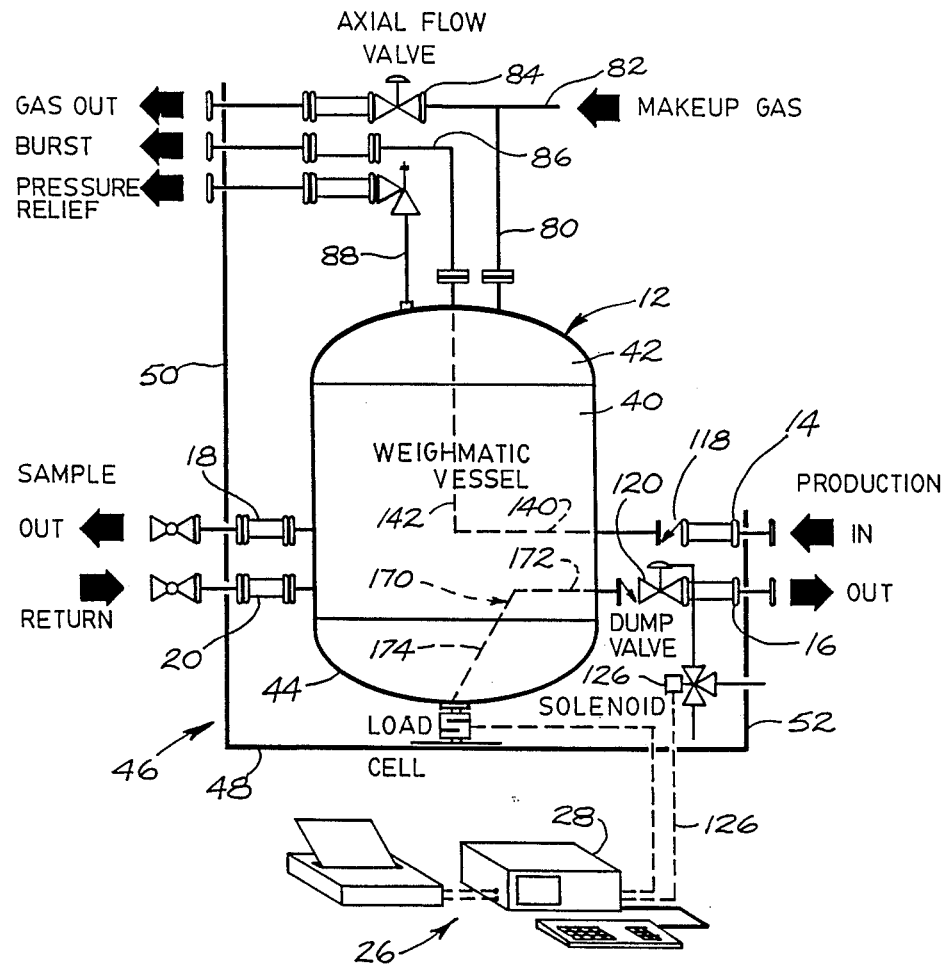
FIG. 4 is a schematic illustration of the pressure vessel illustrated in FIG. 3.

With particular reference to FIG. 1 of the drawings, there is illustrated an apparatus 10 for determining the percentage oil content in the gross production of an oil well where the percentage of solids content of the gross oil production of the well is known. The apparatus comprises a pressure vessel 12 having a well production inlet 14 adapted to be connected to a feeder pipeline (not shown) originating from one or more oil wells and a well production outlet 16 for discharging well production from the vessel. The vessel also includes a sample outlet 18 and a sample return 20 for communicating a sample of the well production in the vessel to a means 22 which subjects the sample to an electromagnetic signal and produces an electrical output signal representative of the percentage water content of the contents of the vessel. A load cell 24 supports the vessel and produces an electrical output signal representative of the weight of the vessel and its contents. Control means 26 (FIG. 4), which includes a microprocessor or computer 28 and various electrically actuated valves described later, is responsive to the output of load cell 24, the electrical output signal representative of the percentage water content of means 22 and a signal representative of the known percentage solids content for producing an output representative of the percentage oil content of oil in the contents of the vessel.

With reference to FIGS. 3 to 7, vessel 12 is comprised of a cylindrical central portion 40, and spherical upper and lower end portions 42 and 44, respectively. Lower end portion 44 is seated upon load cell 24 in coaxial relation thereto while the load cell, inturn, is secured to a base 48 of a support or skid assembly 46. A pair of vertical supports 50 and 52 are secured to and extend vertically from the opposed ends of base 48.

Lower end portion 44 of the vessel is secured to the skid against radial movement but is permitted the limited axial displacement necessary to communicate changes in weight of the vessel to the load cell. To that end, there is provided a pair of lugs 54 secured to and extending vertically from base 48 on diametrically opposed sides of the vertical axis of the load cell with each lug 54 being formed with a vertical slot 56. An associated pair of skirt lugs 58 depend from lower end portion 44 of the vessel on diametrically opposed sides of the longitudinal axis of the vessel with each lug 58 being formed with a vertical slot 60. As shown, one of lugs 54 is associated with one of lugs 58 with their slots being alignable to receive a bolt and nut assembly generally designated by reference numeral 62.

Upper end portion 42 of the vessel is similarly secured to the skid against radial movement but is permitted limited axial displacement necessary to communicate changes in weight of the vessel to the load cell. To that end, there is provided a pair of spaced, suitably reinformed arms 64 extending horizontally from vertical support 50 toward support 52. The free ends of arms 64 are each formed with a vertical slot 66. Slots 66 are arranged to be disposed on diametrically opposed sides of the coaxial axes of vessel 12 and load cell 24. Lugs 68 extend upwardly from upper end portion 42 of the vessel on diametrically opposed sides the longitudinal axis of the vessel with each lug 68 being formed with a vertical slot 70. As shown, each lug 68 is associated with one of arms 64 with their respective slots 66 and 70 being aligned to receive a bolt and nut assembly generally designated by reference numeral 72.

Figure 5:
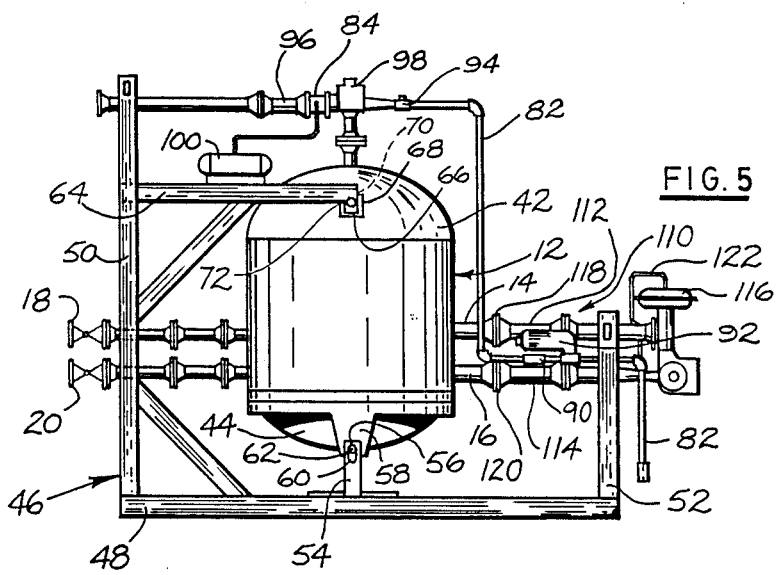
Figure 6:
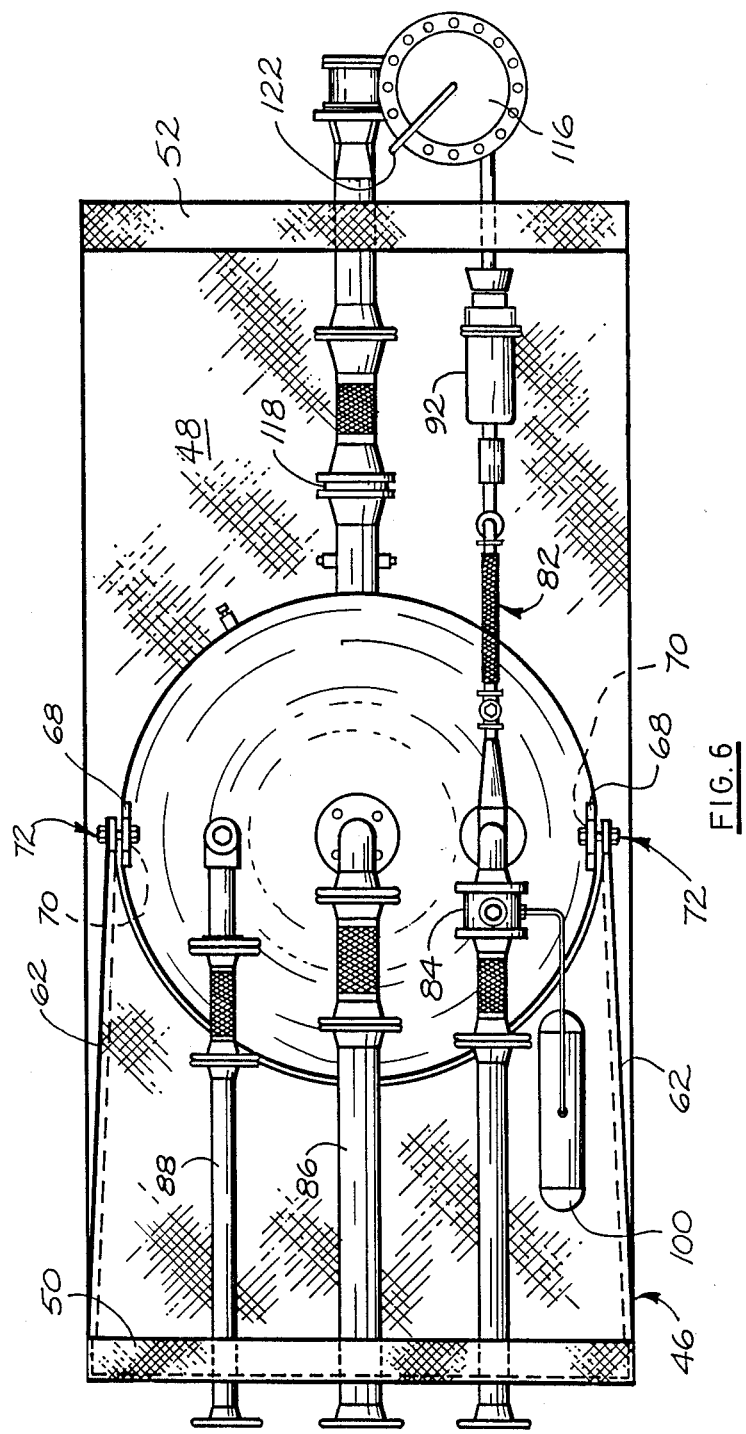

Vessel 12 is pressurized with a suitable make-up gas and maintained at a pressure of about 175 psi in order to accommodate inconsistencies in the output of the well and, more specifically, to provide a means of discharging through outlet 16 excess well production received through inlet 14. Thus, with reference to FIGS. 3 to 5, vessel 12 is provided with a make-up gas inlet 80 communicating with a make-up gas line 82 having an axial flow valve 84 downstream of inlet 80. A burst plate outlet 86 and a pressure relief outlet 88 are provided in accordance with conventional practices to maintain the pressure within the vessel within predetermined, safe operating limits. With reference to FIG. 5, line 82 is arranged to be connected to a supply source of make-up gas (not shown) and includes a ball valve 90 to permit the manual activation of gas flow, a regulator 92 and a check valve 94 to control gas flow. Line 82 is connected to inlet 80 and back pressure line spool 96 at Tee joint 98. Axial flow valve 84 is provided with an independent source of make-up gas, in the form of a nitrogen cylinder 100, to supply gas under pressure to the vessel in the event that the main source of gas is interrupted for some reason.

Figure 7:
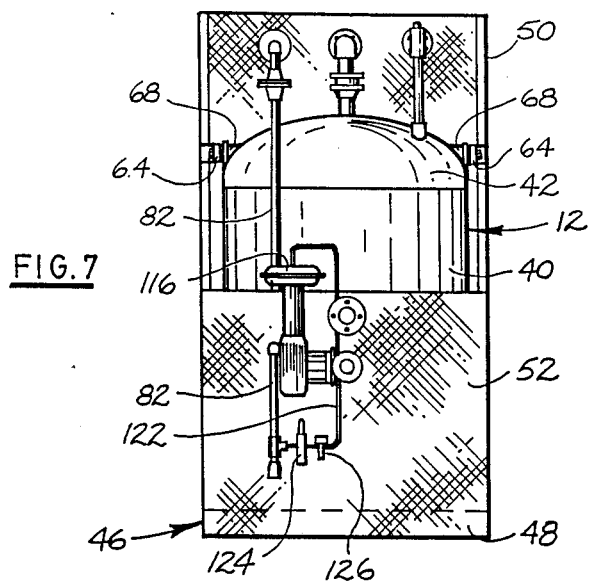
FIGS. 5, 6 and 7 are side, plan and right side views, respectively, of the pressure vessel and a skid assembly for supporting the pressure vessel and associated components.

A well production inlet and outlet valve assembly 110 is comprised of inlet piping spool 112 which is connected to production inlet 14, an outlet piping spool 114 which is connected to production outlet 16, and valve actuator 116. A flapper or check valve 118 is disposed between inlet piping spool 112 and production inlet 14 while a dump valve 120 is disposed between outlet piping spool 114 and production outlet 16. Valve actuator 116 controls valve 120. As best illustrated in FIG. 7, a subsidiary pressure line 122 extends from line 82 to pneumatic valve actuator 116. A pressure regulator 124 and solenoid controlled valve 126 are connected in series in line 122. The solenoid associated with valve 126 is connected with a suitable source of electrical energy via conductor 130 (FIG. 2) which is controlled by computer 28 and, thus, valve 126 permits valve actuator 116 to be controlled from a remote location by an operator or computer. Thus, when solenoid controlled valve 126 is opened, regulator 124 supplies gas under pressure to valve actuator 116, causing valve actuator 116 to operate valve 120. Outlet piping spool 114 is equipped with a back flow valve to prevent back flow into vessel 12. It will be noted from FIG. 2 that load cell 24 is electrically connected to computer 28 via conductor 132.

The internal construction of the vessel will now be described with reference to FIGS. 8A, 8B, 9 and 10. With reference firstly to FIGS. 8A, 8B and 9, a first internal conduit 140 extends radially inwardly of the vessel from inlet 14 to a vertical conduit 142 of enlarged diameter coaxially disposed within vessel 12. The bottom end 144 of conduit 142 is closed by a plate 146. Conduit 142 is secured to the interior walls of the vessel by three radially outwardly extending arms 148 formed of angle iron or other such suitable material. A cap 150 is secured to the upper end 152 of conduit 142 in axially spaced relation to outlet opening 154 thereof to permit well production to spill over the edges of the opening onto a series of trays described below. Conduit 142 is also perorated along its length to provide additional discharge openings 156 to enhance both degassing and mixing of the well production.

A plurality of inclined mixing trays 160 (three are shown) are secured to vertical conduit 142 in vertically spaced, staggered relation beneath cap 150 such that well production flowing over the supper edge 154 and through apertures 156 of conduit 142 flows into the uppermost tray and then cascades into each of the trays positioned therebeneath to further breakup, mix and degas the well production. Like conduit 142, the bottoms of trays 160 may be perforated to further enhance mixing and degassing. While the degree of inclination of mixing trays 160 is not critical, an inclination of 15 degrees has been found to be suitable.

With reference to FIG. 10, an internal discharge conduit 170 is formed with a radially inwardly extending portion 172 connected to well production outlet and an axially downwardly extending portion 174 extending into the lower end portion 44 of vessel 12. Thus, when discharge or dump valve 120 is opened, the pressure within vessel 12 forces well production within the vessel outwardly thereof through conduit 170. Since solids will, over a period of time come out of suspension and will accumulate at the bottom of the vessel, a drain 176 and flushing means 178 are provided for "desanding" the vessel. Flushing means 178 includes a circular fluid conduit or ring 180 concentrically disposed within the lower end portion of the vessel and connected to a source of water via conduit 182. The ring is provided with a plurality of equally angularly spaced, downwardly directed spray nozzles 184. Thus, water may be pumped through conduit 182 and into ring 180 and out nozzles 184 to flush accumulated solids out drain 176.

With reference to FIG. 9, sample outlet 18 is connected to a radially inwardly extending conduit 190 having a pair of arms 192, each having a first laterally outwardly extending portion 194 and a second portion 196 extending at a right angle to the first portion. Each portion 196 is provided with an elongated, downwardly directed intake opening 198.

The sample monitoring apparatus 22 will now be described with reference to FIGS. 1 and 11 to 12. This apparatus provides a means of electromagnetically determining the percentage water content of the well production. As best shown in FIG. 1, a sample flow path includes a first conduit 200 connecting sample outlet 18 and a pump 202 driven by a motor 204 which may be selectively controlled by computer 28 via control line 206 (FIG. 2) if so desired. The flow path further includes a return conduit 208 connecting the high pressure side of the pump to sample return inlet 20 of the vessel. Conduit 208 includes a vertically extending monitoring portion 210 in which the antenna of a suitable commercially available oil/water monitor 212 is disposed. The monitor emits an electromagnetic signal into the fluid stream and a sensor associated with the monitor receives the signal and produces an electrical output representative of the percentage water content of the sample in the flow path. This signal is communicated to computer 28 via conductor 214. Since oil and water normally differ in density, high water content, gravity and low fluid velocities may allow stratification or water to settle out in a horizontal pipe. To avoid inaccurate readings resulting from these factors, the probe is desirably installed in a vertical section of pipe and fluid velocities are maintained at a level which ensures turbulent flow and good mixing of the constituents of the sample.

A sample tap 216 may be provided to allow manual samples to be taken to confirm the accuracy of the results produced by the apparatus. In addition, a sample container 220 may be provided to store a small sample of well production from each of several cycles of operation to allow both manual sampling or the well production and confirming the results of the several cycles by circulating the contents of the sample container through the test loop. To that end, there is provided a first conduit 222 extending from the high pressure side of the pump 202 to container 200 and a second inlet conduit 224 in parellell with the first. The latter conduit is intended or maintenance purposes. The former is provided with a solenoid operated valve 206 having an electrical control line 228 under the control of the computer. A discharge conduit 230 connects container 220 to line 200. A shown in FIGS. 11, 12 and 13, the monitoring apparatus is mounted on a support skid 232.

OPERATION

It will be understood at the outset that the vessel is maintained at a predetermined operating pressure of 175 psi with overpressure conditions being eliminated by the burst plate and pressure relief valves. In addition, once energized, load cell 24 and oil/water monitor 212 continuously produce and transmit to the computer electrical output signals representative of the weight of the vessel and contents and the percentage water content, respectively. Still further pump 202 may operate continuously if so desired. Alternatively, motor 204 may be activated only in that portion of the operating cycle in which the oil/water monitor output is required.

The percentage solids content of each well to be monitored will have been predetermined and input into the computer and each such well will have been assigned a "bottom line" weight and a "top Line" weight. The "bottom line" weight is the weight at which the computer will activate a timer (not shown) while the "top line" weight is the weight at which the computer will stop the timer. Thus, since the difference between the bottom and top line weight will be known in advance for each well, the well flow rate of the well production into the vessel can be readily determined simply by dividing the difference by the time interval required for the weight of the vessel to go from the bottom line weight to the top line weight. Valves 118, 120 will be assumed to be initially closed an valve 226 open.

At an appropriate time, determined by initial conditions input into the computer, the computer will cause a signal to be transmitted to solenoid 126 via line 130 which will cause valve actuator 116 to open well production inlet valve 118. Well production will then enter production inlet 14, conduit 140 and 142, discharge onto trays 160, this serving to degas and agitate or mix the well production, and then fall under gravity to the bottom of the vessel. When the output of the load cell indicates a weight equal to the bottom line weight, the computer will activate a timer. During this time, valve 226 is open and therefore a sample of the well production is allowed to enter sample container 220. When the output of the load cell indicates a weight equal to the top line weight, the computer will deactivate the timer, store the elapsed time and cause a signal to be transmitted to solenoid 126 to close valve 118 and open dump valve 120 to discharge the vessel and a signal via line 228 to close solenoid operated valve 226.

While the vessel was being charged, a sample of the well production was drawn from the vessel via conduits 190 and 192 in the vessel, into the sample flow path by pump 202 and passed oil/monitor 212 whose output the computer read via line 214 and stored. Having thus determined the total well production flow rate, as discussed earlier, obtained a reading of the percentage water content from probe 212 and having in memory the percentage solids contents, it is a simple matter for the computer to convert the three factors to common units and determine the percentage oil content of the well being monitored.

The following example will illustrate the calculations involved. If the recorded flow rate of well production into vessel 12 was determined to be 1625 kilograms per hour, these units can be converted into "cubic meters per day" simply by multiplying 1625 kilograms per hour by 24 hours by 1000 kilograms per cubic meter to provide desired measurement units resulting in 39 cubic meters per day. If probe 212 senses a water content of 27% and the solids content has been predetermined to be 0.25%, the following calculations can be made based upon the previous determination of a flow rate of 39 cubic meters per day:

Daily water flow rate=
  39 cubic meters/day×0.27 (%water)=10.53 cubic meters of water/day
Daily Solids flow rate=
  39 cubic meters/day×0.025 (%solids)=0.097 cubic meters of sand/day
Daily Oil flow rate=
  total daily production−production of water less daily production of solids:
  39−10.53−0.097=28.373 cubic meters per day.

The embodiments of the invention in which an exclusive property or privilege is claimed are defined as follows:

1. A method of measuring the oil content in the gross oil production of an oil well in which the percentage of solids content thereof is known, said method comprising the steps of:
   a. introducing a predetermined weight of well production into said vessel;
   b. determining the weight of the vessel and the time interval required to introduce said predetermined weight of well production into said vessel;
   c. determining the total well production flow rate of said well production into said vessel during said time interval;
   d. electromagnetically determining through the use of an electromagnetic monitoring device the percentage water content in said well production;
   e. determining from said percentage water content the water flow rate into said vessel during said time interval; and
   f. determining from said known percentage solids content the solids flow rate into said vessel during said time interval; and
   g. determining the percentage oil content in said well production by deducting said solids flow rate from said total well production flow rate.

2. A method as defined in claim 1, further including the step of purging said vessel prior to said step of determining an initial weight of a vessel.

3. A method as defined in claim 2, said purging step further including filling said vessel with a gas at a predetermined pressure.

4. A method as defined in claim 2, said purging step further including filling said vessel with an inert gas to a predetermined pressure.

5. A method as defined in claim 1, further including the step of agitating said well production while introducing said predetermined weight of well production into said vessel.

6. A method as defined in claim 1, further including the step of agitating said well production prior to electromagnetically determining the percentage water content in said well production.

7. A method as defined in claim 6, said agitating step comprising introducing said well production into an upper end of said vessel and discharge said well production onto a vertically arrange series of staggered, inclined trays.

8. A method as defined in claim 1, said step of electromagnetically determining the percentage water content in said well production further including taking a sample of said well production, passing said sample passed a static mixer to provide a mixed sample, passing said mixed sample along a vertical flow path and by an electromagnetic probe at an upper end of said vertical flow path.

9. A method as defined in claim 1, further including the step of extracting well production from said vessel following said step of determining the percentage oil content in said well production.

10. A method as defined in claim 9, further including the step removing stratified solids from the bottom of said vessel following said extracting step.

11. A method as defined in claim 10, said removing step including flushing the bottom end of said vessel with water and draining water and solids from the bottom of said vessel.

12. A method for measuring the oil content in the gross oil production of an oil well in which the percentage of solid content thereof is known, said method comprising the steps of:
   a. purging a well production vessel by filling said vessel with a gas to a predetermined pressure;
   b. determining an initial weight of a vessel while pressurized with said gas;
   c. introducing a predetermined weight of well production into said vessel while allowing excess gas to escape and simultaneously agitating said well production while introducing said predetermined weight of well production into aid vessel;
   d. determining the time interval required to introduce said predetermined weight of well production into said vessel;
   e. determining the total well production flow rate of said well production into said vessel during said time interval;
   f. electromagnetically determining through use of an electromagnetic monitoring device the percentage water content in said well production including the steps of passing a sample of well production from said vessel passed a static mixer to provide a mixed sample, passing said mixed sample along a vertical flow path and passed an electromagnetic probe at an upper end of said vertical flow path;
   g. determining from said percentage water content the water flow rate into said vessel during said time interval;
   h. determining from said known percentage solids content the solids flow rate into said vessel during said time interval; and
   i. determining the percentage oil content in said well production by deducting said solids flow rate and said water flow rate from said total well production flow rate;

j. extracting well production from said vessel; and k. removing stratified solids from the bottom of said vessel following said extracting step, including flushing the bottom end of said vessel with water and draining water and solids from the bottom of said vessel.

13. A method as defined in claim 12, said step of simultaneously agitating said well production including introducing said well production into an upper end of said vessel and discharging said well production onto a vertically arranged series of staggered, inclined trays.

14. An apparatus for measuring the production of oil in the gross production of an oil well where the percentage of solids content of said gross oil production of said well is known, said apparatus comprising:
   a. a pressure vessel having a well production inlet adapted to be connected to a feeder pipeline originating from one or more oil wells and a well production outlet for discharging well production from said vessel;
   b. means for producing an electrical output signal representative of the weight and contents of said vessel;
   c. means for transmitting a predetermined electromagnetic signal into a sample of the contents in said vessel, receiving a return signal and producing an electrical output signal representative of the percentage water content of said contents of said vessel;
   d. means for determining the time interval required to admit a predetermined weight of well production into said vessel and producing a signal representative of fluid flow rate of said predetermined weight of well production into said vessel; and
   e. means responsive to said signal representative of fluid flow rate, said electrical output signal representative of the percentage water content and a signal representative of said known percentage solids content for producing an output representative of the percentage oil content of oil in said contents of said vessel.

15. An apparatus as defined in claim 14, further including means for pressurizing said vessel with a gas at a predetermined pressure prior to admitting said well production into said vessel.

16. An apparatus as defined in claim 14, further including means for degassing said well production while admitting said well production into said vessel.

17. An apparatus as defined in claim 14, further including means for agitating said well production while admitting said well production into said vessel.

18. An apparatus as defined in claim 16, wherein said degassing means said well production including:
   a discharge head communicating with said well production inlet for discharging said well production at an upper end of said vessel;
   a plurality of vertically spaced, inclined mixing trays in said vessel beneath said discharge head whereby well production discharged from said discharge head cascades downwardly sequentially from an uppermost tray to a lowermost tray and intermediate trays disposed therebetween.

19. An apparatus as defined in claim 14, further including means for discharging the contents of said vessel.

20. An apparatus as defined in claim 19, said discharging means including first discharging means including a first outlet for discharging fluid contents of said vessel and second discharging means including a second outlet means for discharging settled solids contents from said vessel.

21. An apparatus as defined in claim 20, said second discharging means including means for flushing at least the bottom end of said vessel with a fluid and said second outlet means being a drain disposed at the bottom of said vessel.

22. An apparatus as defined in claim 14, including a sample fluid flow path extending from said vessel, said electromagnetic signal producing means having antenna means disposed in said flow path.

23. An apparatus as defined in claim 22, said flow path including agitating means upstream of said electromagnetic signal producing means for thoroughly mixing said sample.

24. An apparatus as defined in claim 14, said means for producing an electrical output signal representative of weight being a load cell supporting said vessel.

25. An apparatus as defined in claim 22, further including first electrically actuated valve means for admitting well production into said vessel, second electrically actuated valve means for discharging well production from said vessel once a predetermined weight of production has entered said vessel, third electrically actuated valve means for admitting pressurized gas into said vessel; and fourth electrically actuated valve means for admitting a sample of said well production into said sample flow patch, and control means for controlling each said valve means in predetermined timed sequence.

26. An apparatus as defined in claim 25, said control means including a microprocessor.

27. The apparatus as defined in claim 22, wherein said electromagnetic signal producing means is positioned in a downsized section of said feeder pipeline downstream of said static mixer.

28. An apparatus as defined in claim 27, wherein said electromagnetic signal producing means is disposed in a vertical portion of said flow path.

29. An apparatus as defined in claim 28, wherein the flow rate of said sample in said vertically disposed portion of said flow path is about 5 feet per second or greater.

30. The apparatus as defined in claim 20, wherein said flushing means including a circular water intake pipe disposed within said vessel adjacent the bottom end thereof, said water intake pipe having a plurality of spray nozzles disposed thereabout for providing a plurality of downwardly directed sprays and being adapted to be connected to a water source external of said vessel.

31. An apparatus for measuring the production of oil in the gross production of an oil well where the percentage of solids content of said gross soil production of said well is known, said apparatus comprising:
   a. a support;
   b. a load cell secured to said support and having a vertical axis, said load cell being adapted to produce an electrical signal representative of the weight of a body supported thereon;
   c. a pressure vessel having a longitudinal axis, said vessel being secured to and supported by said load cell in coaxial relation thereto, said support having means for maintaining said vessel in coaxially disposed on said load cell while permitting said vessel to move vertically on said load cell in response to changes in weight of said vessel, said vessel including:

i. a well production inlet adapted to be connected to a feeder pipeline from one or more oil wells;

ii. first electrically controlled valve means associated with said inlet for admitting well production into said vessel;

iii. a well production outlet for discharging well production from said vessel;

iv. second electrically controled valve means associated with said outlet for discharging well production from said vessel;

v. a sample outlet for removing a sample of well production from said vessel;

vi. third electrically controlled valve means associated with said inlet for discharging a sample of said well production from said vessel; and vii. pressure relief means for maintaining the fluid pressure within said vessel below a predetermined pressure;

d. means disposed within said vessel for separating gases from well production, said means including:

i. a discharge head communicating with said well production inlet for discharging said well production at an upper end of said vessel; and ii. a plurality of vertically spaced, inclined mixing trays in said vessel beneath said discharge head whereby well production discharged from said discharge head cascades downwardly sequentially from an uppermost tray to a lowermost tray and intermediate trays disposed therebetween;

e. means for charging said vessel with a gas a predetermined pressure;

f. fourth electrically controlled valve means associated with said charging means for admitting gas under pressure into said vessel;

g. means for subjecting a sample of the contents in said vessel to a predetermined electromagnetic signal and producing an electrical output signal representative of the percentage water content of said contents of said vessel, said subjecting means including:

i. conduit means defining a sample fluid flow path extending from said vessel and communicating with said sample outlet;

ii. means for producing said electromagnetic signal, said electromagnetic signal producing means having antenna means disposed in said flow path for transmitting said signal and receiving a return signal and producing said electrical output signal representative of the percentage water content of said well production; and iii. pump means in said conduit means for pumping said sample under pressure through said flow path; and h. microprocessor means for controlling said electrically actuated valve means in predetermined timed sequence including:

i. opening said fourth valve means for admitting gas under pressure into said vessel and closing said fourth valve means at a predetermined pressure;

ii. reading the electrical output of said load cell whereby to determine the initial weight of said vessel;

iii. opening said first valve means for admitting well production into said vessel;

iv. closing said first valve means when a predetermined weight of well production has been admitted into said vessel;

v. determining the total production flow rate of said predetermined weight of well production into said vessel;

vi. opening said third valve means and said activating said pump means to cause a sample of said well production in said vessel to flow through said flow path;

vii. reading said electrical output signal representative of the percentage water content of said contents of said vessel, determining water flow rate into said vessel and closing said third valve means;

viii. determining the oil production of well production by deducting said water flow rate and the solids content flow rate derived from said known percentage solids content from said total production flow rate;

ix. opening said second valve means for discharging well production from said vessel; and x. activating a desanding means for removing settled solids in said vessel.

* * * * *